United States Patent
Vardi (10) Patent No.: US 11,672,755 B2
(45) Date of Patent: Jun. 13, 2023

(54) EXTENDED RELEASE PLASTIC FORMULATION

(71) Applicant: WANKA TANKA LTD., Beit Shean (IL)

(72) Inventor: Amnon Vardi, Ram On (IL)

(73) Assignee: WANKA TANKA LTD., Beit Shean (IL)

( * ) Notice: Subject to any disclaimer, the term of this patent is extended or adjusted under 35 U.S.C. 154(b) by 0 days.

(21) Appl. No.: 17/789,530

(22) PCT Filed: Dec. 31, 2020

(86) PCT No.: PCT/IL2020/051370
§ 371 (c)(1),
(2) Date: Jun. 28, 2022

(87) PCT Pub. No.: WO2021/137240
PCT Pub. Date: Jul. 8, 2021

(65) Prior Publication Data
US 2023/0048900 A1    Feb. 16, 2023

Related U.S. Application Data

(60) Provisional application No. 62/955,461, filed on Dec. 31, 2019.

(51) Int. Cl.
| | | |
|---|---|---|
| *A61K 9/00* | (2006.01) |
| *A61K 47/32* | (2006.01) |
| *A61K 47/44* | (2017.01) |
| *A61K 47/10* | (2017.01) |
| *A61K 47/34* | (2017.01) |
| *A61K 31/198* | (2006.01) |
| *A61K 31/737* | (2006.01) |
| *A61K 31/10* | (2006.01) |
| *A61K 38/39* | (2006.01) |
| *A61K 31/12* | (2006.01) |
| *A61K 36/53* | (2006.01) |
| *A61K 31/714* | (2006.01) |
| *A61K 31/405* | (2006.01) |
| *A61K 36/88* | (2006.01) |
| *A61K 36/38* | (2006.01) |
| *A61K 31/197* | (2006.01) |
| *A61K 31/7008* | (2006.01) |

(52) U.S. Cl.
CPC ............ *A61K 9/0017* (2013.01); *A61K 31/10* (2013.01); *A61K 31/12* (2013.01); *A61K 31/197* (2013.01); *A61K 31/198* (2013.01); *A61K 31/405* (2013.01); *A61K 31/7008* (2013.01); *A61K 31/714* (2013.01); *A61K 31/737* (2013.01); *A61K 36/38* (2013.01); *A61K 36/53* (2013.01); *A61K 36/88* (2013.01); *A61K 38/39* (2013.01); *A61K 47/10* (2013.01); *A61K 47/32* (2013.01); *A61K 47/34* (2013.01); *A61K 47/44* (2013.01)

(58) Field of Classification Search
None
See application file for complete search history.

(56) References Cited

U.S. PATENT DOCUMENTS

| | | | | |
|---|---|---|---|---|
| 6,372,242 B1 * | 4/2002 | Gutierrez | ............... | A01N 25/34 |
| | | | | 514/579 |
| 7,910,122 B2 * | 3/2011 | Sirinyan | ................ | A01N 51/00 |
| | | | | 424/405 |
| 2009/0155326 A1 | 6/2009 | Mack | | |
| 2012/0315454 A1 | 12/2012 | Wang | | |

FOREIGN PATENT DOCUMENTS

| | | | | |
|---|---|---|---|---|
| WO | 2010/075298 | 7/2010 | | |
| WO | WO-2010075298 A2 * | 7/2010 | ............. | A61K 31/56 |
| WO | 2021005606 | 1/2021 | | |

* cited by examiner

*Primary Examiner* — Melissa S Mercier
(74) *Attorney, Agent, or Firm* — JMB Davis Ben-David (57) ABSTRACT

A plastic material for extended release of a bio-active agent, the plastic material comprising a structural polymer, at least one bio-active ingredient embedded within the structural polymer as solid islands, a liquid binding material embedded within the structural polymer as granules, and a carrier liquid absorbed within the liquid-absorbent material. The carrier liquid may be sufficiently non-compatible with the structural polymer so that at least a portion of the carrier liquid is released from the liquid-absorbent material through the structural polymer to an outer surface of the plastic material over a period of time, such as a week or more, a month or more, or about three months. The bio-active agent comprised in the at least one bio-active ingredient may be sufficiently soluble in the carrier liquid at room or body temperature so that the carrier liquid released to the outer surface comprises the bio-active agent in solution.

20 Claims, 2 Drawing Sheets

EXTENDED RELEASE PLASTIC FORMULATION

RELATED APPLICATIONS

This is the U.S. National Stage of International Patent Application No. PCT/IL2020/051370 filed Dec. 31, 2020, which claims priority to U.S. Provisional Patent Application No. 62/955,461 filed Dec. 31, 2019, the disclosure of which is incorporated herein by reference.

BACKGROUND

Administrable bio-active agents, such as therapeutic agents and nutritional supplements, can be administered into the body in multiple different routes. While oral administration is a common route, this route has various drawbacks such as first-pass metabolism, wherein the gastric environment and liver metabolizes the bio-active agent so that its concentration is greatly reduced before it reaches systemic circulation. In addition, oral administration may be ineffective in patients who are experiencing nausea and vomiting. Another issue with oral administration is that patients absorb the bio-active agent as a bolus that results in peaks and troughs of systemic concentration in the bloodstream that may cause unwanted side effects and unevenness of desired effects over time.

Transdermal delivery is another potential route for administration as it circumvents the gastric system increasing bioavailability. The skin serves as an effective barrier to microbes and foreign molecules, however, small molecules can diffuse across the skin. While creams and lotions may be used as a way of administration, they have the drawback of being short-acting and may be accidentally rubbed or washed off the skin resulting in difficulty in achieving consistent or effective bloodstream concentration. Therefore, a need exists for a method of transdermal delivery of bio-active agents over an extended period of time, by way of example, over a period of a week, a month, or up to several months.

SUMMARY

An aspect of the disclosure relates to solid compositions comprising a plastic material embedded with one or more bio-active agents such as therapeutic agents and nutritional supplements, the plastic material being formulated for an extended release of the embedded one or more bio-active agents.

For convenience of presentation, a plastic matrix embedded with one or more bio-active agents in accordance with an embodiment of the invention may be referred to herein as an extended release plastic matrix (ERPM).

Throughout the specification, "extended release" refers to the release of an agent from a material and/or into the bloodstream of a subject over an extended period of time, by way of example about a week, about two weeks, about a month, or over a month. The term may be used interchangeably with "slow release" or "sustained release".

In an embodiment of the disclosure, an ERPM comprises a structural polymer, a liquid-binding material embedded within the structural polymer, a carrier liquid absorbed within the liquid-binding material, and at least one bio-active ingredient comprising or consisting of a bio-active agent embedded optionally as solid islands within the structural polymer.

In an embodiment of the disclosure, the carrier liquid is partially absorbable into and partially non-compatible with the structural polymer and is capable of dissolving the bio-active agent at room or body temperature.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

An aspect of the disclosure relates to a providing a ERPM comprising a structural polymer and one or more bio-active ingredients embedded within the structural polymer, wherein bio-active agents comprised in the one or more bio-active ingredients are released through a surface of the ERPM for an extended period of time. The release of the bio-active agent by the ERPM may be at a therapeutically effective rate in the context of transdermal absorption.

As used herein, a bio-active ingredient refers to a synthetic or natural substance that consists of or comprises a bio-active agent, which may be a therapeutic agent or a nutritional supplement.

Figure 1:
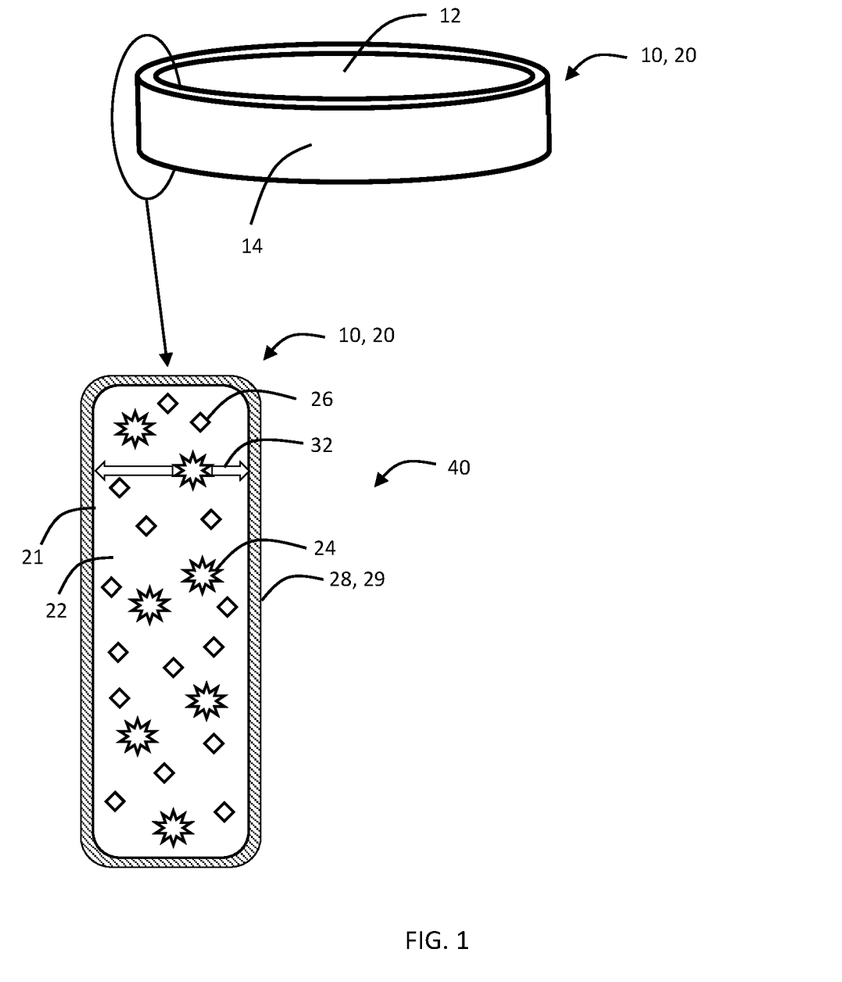
FIG. 1 schematically shows a wristband-shaped ERPM in accordance with an embodiment of the disclosure.

Reference is made to FIG. 1, schematically showing a wristband-shaped wearable apparatus 10 consisting of an ERPM 20 in accordance with an embodiment of the disclosure. Inset 40 schematically shows a magnified cross section of ERPM 20, which is optionally formulated to comprise a structural polymer 22, granules 24 of liquid-binding material embedded within structural polymer 22, a carrier liquid (not shown) absorbed within the granules, and at least one bio-active ingredient embedded as islands 26 within the structural polymer.

Respective constituents of the carrier liquid and structural polymer 22 may be selected so that the carrier liquid is at least partially non-compatible with the structural polymer 22. As used herein, a give carrier liquid may be characterized as being non-compatible with a given structural polymer if the structural polymer does not readily absorb the carrier liquid, and/or at least a portion of the carrier liquid compounded with the structural polymer is spontaneously released or extruded out from the structural polymer. The carrier liquid may additionally be characterized by being capable of at least partially dissolving islands 26 at room or body temperature. Partially dissolving as used herein means that, if a given bio-active ingredient is a complex or compound substance, by way of example dried plant matter that comprises a bio-active agent among other substances, the carrier liquid is capable of dissolving at least the bio-active agent.

For an ERPM 20 formulated with a given structural polymer and a given bio-active ingredient, the composition of the carrier liquid may be selected so the carrier liquid is partially absorbable and partially non-compatible with the structural polymer, and is capable of dissolving a bio-active agent comprised in the bio-active ingredient. Without being bound by theory, as a result of the above properties (partial non-compatibility with the structural polymer and ability to dissolve the bio-active agent), the carrier liquid is advantageously operable within ERPM 20 to: (a) migrate from granules 24 of the liquid-binding material through structural polymer 22 and contact islands 26; (b) dissolve a bio-active agent comprised in islands 26 to form a bio-active solution 28; and (c) continue migration and be released to outer surface 21 of ERPM 20 to form an outer liquid layer 29 of bio-active solution 28. The migration of the carrier liquid from granules 24 through structural polymer 22 and eventual release onto surface 21 of ERPM 20 as a constituent of bio-active solution 28 is schematically represented with block arrows 32.

Without being limited by theory, it will be appreciated that the above-noted migration of the carrier liquid and release of bio-active solution 28 from outer surface 21 is driven by a concentration gradient of the carrier liquid within structural polymer 22, as explained hereinbelow. Initially, following manufacture of ERPM 20, the carrier liquid may be present only at granules 24 and not elsewhere in ERPM 20, and the concentration gradient results in net migration from granules 24 into structural polymer 22, which results in the carrier liquid contacting islands 26, dissolving at least one bio-active agent present in the islands, and being released at outer surface 21 as bio-active solution 28. However, once sufficient bio-active solution 28 has been released, the concentration of carrier liquid at outer surface 21 and at granule 24 become balanced so that net release of carrier liquid onto outer surface 21 becomes substantially null. As a result, without being limited by theory, ERPM 20 advantageously does not continue to release excess bio-active solution 28 during storage once a threshold amount of outer liquid layer 29 has formed. Similarly, without being limited by theory, portions of outer surface 21 that does not make contact with skin or other absorbent surfaces advantageously does not release excess bio-active solution 28 that would cause discomfort or staining. The release of bio-active solution being responsive to the relative concentration of the carrier liquid at outer surface 21 and granules 24 also allows, without being limited by theory, for contact-sensitive release of bio-active solution 28, in which bio-active solution 28 is selectively released at portions of outer surface 21 that make contact with skin or other absorbent surfaces. Without being limited by theory, contact of ERPM 20 on skin leads to transdermal absorption of bio-active solution 28 present at outer liquid layer 29, which introduces a concentration gradient of the carrier liquid between the contacted portion of outer surface 21 and granules 24, thus driving further migration of carrier liquid from granules 24 to the contacted portion of outer surface 21. This further migration of the carrier liquid leads to additional bio-active solution 28 being selectively released at the contacted portion, that is, in a contact-dependent manner.

ERPM 20 may be formulated so that contact-sensitive release of bio-active solution 28 is at a therapeutically effective rate for transdermal absorption for at least one week, at least two weeks, or about a month or more. The extended contact-sensitive release of bio-active solution 28 from the ERPM advantageously allows the wearer of wearable apparatus 10 comprising or shaped from the ERPM to wear the apparatus for extended periods of time and benefit from the extended release before requiring replacement.

As shown in FIG. 1, granules 24 are optionally embedded within structural polymer 22 in a substantially even distribution. Islands 26 may also be embedded within the structural polymer in a substantially even distribution.

Structural polymer 22 optionally comprises one or more of a flexible polymer or an elastomer with viscoelastic properties. The one or more polymers comprised in the structural polymer may be non-toxic and appropriate for extended periods of external contact on a skin of a human or animal subject. Optionally, the structural polymer comprises one or more selections from a group consisting of: a polyolefin such as a polyethylene (PE), a polyvinyl chloride (PVC), a polyurethane (PU), an ethylene vinyl acetate (EVA), a polyolefin elastomer, and a synthetic rubber. The PE optionally comprises a low-density polyethylene (LDPE), a linear low-density polyethylene (LLDPE), or combinations thereof. The structural polymer may comprise polyurethane such as a thermoplastic polyurethane (TPU). Optionally, the synthetic rubber comprises a styrene-butadiene rubber, also known as a Poly(styrene-butadiene-styrene) rubber ("SBS rubber"), and/or a silicone rubber such as polysiloxane. In an embodiment of the disclosure, the structural polymer is formulated as an adhesive polymer or a non-adhesive polymer. In a more particular embodiment, the structural polymer may comprise PEs optionally selected from the group consisting of: a LLDPE, a LDPE, and a PE elastomer (by way of example one or more Dowlex™ resins). Optionally, the structural polymer comprises or consists of a LLDPE, a LDPE, and a PE elastomer. The polyolefin elastomer may be an ethylene-octene elastomer, an ethylene-butene elastomer, or an ethylene-hexene elastomer (by way of example one or more of the Dow Engage™ or the Sabic Fortify™ polyolefin elastomers).

Optionally, the structural polymer is formulated to be hydrophobic, characterized by a "contact angle" of larger than 90 degrees, as exhibited by a drop of water on a flat, solid surface of the structural polymer.

Granules 24 of liquid-binding material may comprise one or a combination of two or more selections from the group consisting of: a silica gel, a fumed silica (also known as pyrogenic silica), a diatomite, a carbon black, and an activated carbon. Silica gel is a porous silicon dioxide that is available in a wide variety of grain sizes. Fumed silica consists of microscopic droplets of amorphous silica fused into branched, chainlike, three-dimensional secondary particles which then agglomerate into tertiary particles having a high surface-to-volume ratio and typically having a size of about 5 nm to 50 nm. Diatomite is a naturally occurring fossilized remains of diatoms composed mostly or entirely from silica and is characterized by porosity and high surface area. Diatomite is typically in the form of a powder having a particle size ranging from less than 3 µm to more than 1 mm, but typically 10 µm to 200 µm. Activated carbon typically consists of charcoal that has been treated with either a combination of heat and pressure, or with strong acid or base followed by carbonization, to make it highly porous. Carbon black is a material produced by the incomplete combustion of heavy petroleum products, which is a form of paracrystalline carbon that has a high surface-area-to-volume ratio, but typically lower than that of activated carbon. Subtypes of carbon black include acetylene black, channel black, furnace black, lamp black and thermal black.

Additionally or alternatively, the liquid-binding material of granules 24 comprises a polymer appropriate for use as a structural polymer, which is formed in a porous form using appropriate manufacturing procedures known in the art. The porous polymer may comprise a polyethylene vinyl acetate (PEVA) or a polyolefin by way of example a LDPE. Optionally, the porous polymer is formulated to have a higher melting point compared to the structural polymer used for ERPM 20 so that the pores of the porous polymer are not substantially degraded or eliminated during incorporation into the ERPM, or if the ERPM is formed, for example by injection molding, into wearable apparatus 10.

The granules may depend on how the granules are manufactured, and may be in one or more of a variety of shapes, such as spherical, flattened spherical, cylindrical, or irregular. Granules 24 may have a maximum transverse cross-sectional distance, which may be a diameter for granules that are substantially spherical, of between about 1 nm and about 5 mm. The granules are optionally in the form of a powder, with transverse cross-sectional distance of each granule being between about 1 nm and about 10 microns. Where the granules comprise a porous polymer, the transverse cross-sectional distance of each granule may be between 0.5 mm and 5 mm.

When granules 24 of carrier liquid-infused liquid-binding material is compounded with structural polymer 22, the resulting embedded granules optionally functions as a reservoir of carrier liquid. Optionally, granules 24 is compounded into structural polymer 22 that has been softened with heat during manufacture of a ERPM. Granules 24 may be in an amount sufficient to absorb the carrier liquid prior to compounding with structural polymer 22. By way of example, 1 gram of fumed silica may be capable of absorbing up to 10 to 20 grams of oil, while 1 gram of porous polymer may be capable of absorbing up to 3 or 4 grams of oil. Thus, the relative content of granules 24 in ERPM 20 may depend on which liquid-binding material is used.

Carrier liquid infused in granules 24 may comprise between 5-40% of the total composition by weight of ERPM 20.

Optionally, the carrier liquid comprises one or more non-volatile oils, which are characterized with a vapor pressure such that the oil does not substantially vaporize at about room temperature and at about standard atmospheric pressure. Optionally, the one or more non-volatile oils are (1) compatible as solvent for a bio-active agent comprised in islands 26; (2) liquid at room temperature and/or body temperature and (3) compatible with topical administration on human skin. Optionally, the non-volatile oil comprises a paraffin oil (which may also be referred to in the art as a mineral oil) and/or one or more plant-derived oils, by way of example hempseed oil, palm oil, canola oil, linseed oil, sunflower oil, rapeseed oil, cocoa butter, olive oil, rice bran oil. Paraffin oil has been demonstrated to promote skin permeability through lipid fluidization within the outer layer of the skin (the stratum corneum) and therefore, without being bound by theory, the paraffin oil may be comprised in the carrier liquid in order to enhance transdermal penetration of bio-active agents into a skin of a subject that is in contact with ERPM 20.

Additionally or alternatively, the carrier liquid comprises a volatile oil, which as used herein is characterized with a vapor pressure such that the oil has a tendency to vaporize at about room temperature and at about standard atmospheric pressure. Without being bound by theory, addition of a volatile oil in the carrier liquid enhances release of the carrier liquid onto outer surface 21 because evaporation of the volatile oil from the outer surface creates a concentration gradient that will draw more carrier liquid, together with bio-active agent dissolved into the carrier liquid, toward the surface. Optionally, the volatile oil comprises or is comprised in a natural extract or essential oil added to provide an odor generally accepted to be pleasant. A natural extract or essential may be a mixture of volatile oils and non-volatile oils. Examples of natural extracts that may be incorporated may include but are not limited to the following essential oils: Lavender oil, Valerian oil, Geranium oil, Passiflora Edulis Seed Oil and Chamomile oil.

Additionally or alternatively, the carrier liquid optionally comprises one or more selections from the group consisting of: a chlorinated paraffin, a triacetin, a naphtenic hydrocarbon, an aliphatic hydrocarbon, a dioctyl terephthalate (DOTP), a diisononyl phthalate (DINP), and an epoxidized triglyceride. The epoxidized triglyceride may be an epoxidized vegetable-derived oil such as an epoxidized soybean oil (ESBO), an epoxidized palm oil, an epoxidized canola oil, an epoxidized linseed oil, an epoxidized sunflower oil, an epoxidized rapeseed oil, an epoxidized cocoa butter, an epoxidized olive oil, and an epoxidized rice bran oil, amongst others Additionally or alternatively, the carrier liquid comprises glycerol.

In an embodiment of the disclosure, an ERPM at least initially comprises one or more bio-active ingredients comprising or consisting respectively of bio-active agents such that the one or more bio-active ingredients is between 0.1% and 40% of the initial total weight of the ERPM (% w/w), or between 0.5% w/w and 2.5% w/w of the initial total weight of the ERPM.

In an embodiment of the disclosure, a bio-active ingredient embedded as islands within an ERPM may be a therapeutic agent and/or a nutritional supplement having nutritional and/or therapeutic value once administered to a subject. The bio-active ingredient and/or the bio-active agent comprised therein may be in solid form at standard atmospheric pressure and at room temperature, about 20 degrees Celsius (deg. C), and/or at body temperature, about 37 deg. C, and is at least partially soluble in an appropriate carrier liquid under the same temperature and pressure conditions.

The bio-active ingredient may be a plant- or animal-derived substance, mineral, chemical composition or a combination thereof comprising or consisting of a bio-active agent. The bio-active agent may be suitable for transdermal administration and may have one or more of the following properties: an analgesic property, an anti-inflammatory property, an antioxidant property, and a calming or relaxing property. Optionally, the subject is an animal subject or a human subject.

A bio-active ingredient comprising or consisting of a bio-active agent having an analgesic property may be selected from the group consisting of an aloe vera, a methylsulfonylmethane (MSM), an emu oil, a menthol, a glucosamine, a chondroitin, a capsaicinoid, arnica, coriander, Roman chamomile, willow bark, feverfew, St. John's wort, kava kava, nettle leaf, acetylsalicylic acid, Bala, black cohosh, black snakeroot, bugbane, squawroot, bupleurum, calendula, camphor, cayenne, devil's claw root, evening primrose oil, ginger, gotu kola, ginkgo, juniper, lavender, licorice, marjoram, meadow sweet, passion flower, quercetin, salicinum, wild yam, wintergreen, wood betony, wormwood and combinations thereof.

A bio-active ingredient comprising or consisting of a bio-active agent having an anti-inflammatory property may be selected from the group consisting of an aloe vera, a methylsulfonylmethane (MSM), an emu oil, a chondroitin, a glucosamine, a capsaicinoid, an arnica, a grape seed, a coriander, a marigold, a nettle leaf, a Roman chamomile, a blue-bottle, a St. John's wort, a willow bark, a witch hazel, a feverfew, a barley grass, a black cohosh, a black snakeroot, a bugbane, a squawroot, a Boswellia, a borage, a bromelain, a burdock, a calendula, a cayenne, a dandelion, a devil's claw root, DHEA (dehydroepiandosterone), an Echinacea, an elderflower, an evening primrose, a flaxseed, a ginkgo, a ginger, a ginseng, a Hawthorne, a kaempferol, a licorice, a life root, a golden Senecio, a squaw weed, a golden groundsel, a cocash weed, a coughweed, a ragwort, a golden ragwort, a marjoram, a meadow sweet, a quercetin, a turmeric, a curcumin, a wild yam, a wormwood, a yucca and combinations thereof.

A bio-active ingredient comprising or consisting of a bio-active agent having an antioxidant property may be selected from the group consisting of a chondroitin, a vitamin C, a grape seed, a St. John's wort, a coriander, a barley grass, a bilberry, an Echinacea, a garlic, a ginger, a ginkgo, a ginseng, a grape seed proanthocyanidin extract, a green tea, a Hawthorne, a lemon balm, a milk thistle, an oregano, a peppermint, a pomegranate extract, a purslane, a pycnogenol, a rosemary, a schizandra, a wuweizi, a wurenchun, a trilinolein, a sanchi, a turmeric, a curcumin and combinations thereof.

A bio-active ingredient comprising or consisting of a bio-active agent having a calming or relaxing property is selected from the group consisting of a MSM, a kava kava, a Roman chamomile, a feverfew extract, a St. John's wort, a bee pollen, a bergamot, a black cohosh, a black horehound, a bugleweed, a California poppy, a clary sage, a cowslip, a damiana, a DHEA, a geranium, a ginseng, a gotu kola, a grapefruit, a hyssop, a Jamaican dogwood, a lady's slipper, a lavender, a lemon balm, a licorice, a linden, a lobelia, a mate, a mistletoe, a motherwort, a mugwort, an oat straw, a passion flower, a peppermint, a rosemary, a skullcap, a valerian root, a vervain, a wild lettuce, a wood betony, a cannabis flower or bud, and combinations thereof.

Many of the optional bio-active ingredients listed herein are herbal ingredients. In a case where the bio-active ingredient is an herbal ingredient, the bio-active ingredient may be comprised in an ERPM in the form of a powdered plant matter, or a powdered extract thereof that is enriched in a desired bio-active agent comprised in the plant matter. The extract may be prepared by soaking the natural product in a liquid medium, such as water, alcohol, or a volatile oil, then evaporated to form a dried powder.

Additionally or alternatively, a bio-active ingredient comprised in the ERPM may be one or more of the following: a collagen, a coenzyme Q, or a vitamin. The vitamin may be a vitamin A, a vitamin B, or a vitamin C. The vitamin B may be one or a combination of two or more of a thiamine (B1), a riboflavin (B2), a niacin (B3), a pantothenic acid (B5), a pyridoxine (B6), a biotin (B7), a folate (B9) and a cobalamin (B12).

As shown in FIG. 1, ERPM 20 is molded into a wearable apparatus 10 having a wristband shape suitable for being worn on a wrist of a subject. However, in other embodiments of the disclosure, ERPM 20 may be molded into other wearable shapes such as a necklace, a shape suitable for being worn around an arm or leg of a subject, a patch, an anklet, a collar, or a shoe insert. Optionally, the ERPM 20 is molded to be shaped like, and function as, a watch strap.

Figure 2:
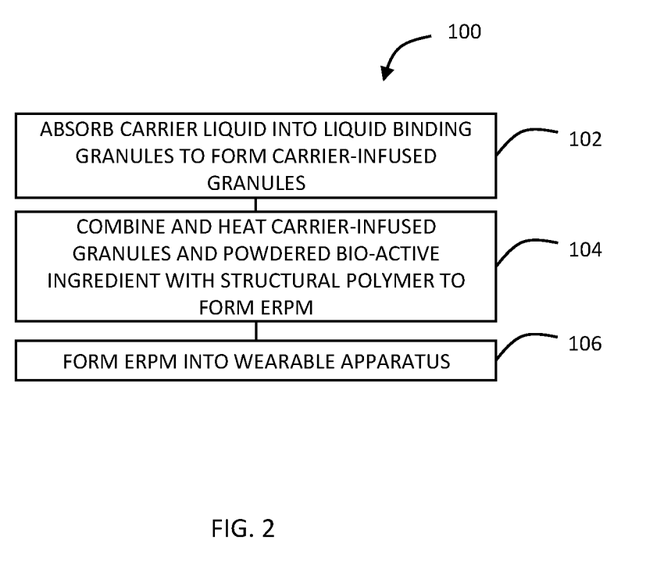
FIG. 2 shows a flowchart of a method of producing an ERPM in accordance with an embodiment of the disclosure.

ERPM 20 may be produced according to the following method 100. In a block 102, a carrier liquid is combined with granules 24 of liquid binding material and mixed until the carrier liquid becomes substantially or fully absorbed into the granules, resulting in carrier-infused granules. In a block 104, carrier-infused granules 24 and at least one bio-active ingredient in granulated or powder form are compounded with structural polymer 22. The compounding may be performed in a heated environment at a temperature sufficiently high to melt structural polymer 22 but not the granules 24 or the at least one bio-active ingredient, optionally between 110 deg. C and 160 deg. C, to form ERPM 20 in liquid form, then optionally cooled down. Optionally, the ERPM is formed in a compounding extruder.

In a block 106, the ERPM optionally is formed into a desired shape to form wearable apparatus 10. The ERPM may be granulated to form ERPM granules, then injection molded in a mold. It will be appreciated that the ERPM granules may be shaped into a wide variety of shapes to form different wearable apparatuses, by way of example, wristbands (as shown in FIG. 1), anklets, patches, shoe inserts, necklaces, and the like. It will also be appreciated that the exact temperatures to which the structural polymer or ERPM is heated in blocks 104 and 106 depend on the polymer(s) comprised in structural polymer 22, as well as granules 24 and the at least one bio-active ingredient comprised in a given ERPM.

Exemplary, non-limiting, example formulations for ERPM 20 are provided hereinbelow. In each of the example formulations below, a carrier liquid migrates from granules 24 of the liquid-binding material through structural polymer 22 and contact islands 26 of a bio-active ingredient, dissolve a bio-active agent comprised in the islands to form a bio-active solution 28, and continue migration to be released to outer surface 21 of ERPM 20 to form an outer liquid layer 29 of the bio-active solution. Moreover, in a wearable apparatus comprising or consisting of one of the example ERPMs described hereinbelow, the bio-active solution 28 is released to the surface in a contact-sensitive manner, responsive to absorption of the bio-active solution away from to outer surface of the ERPM, by way of example transdermal absorption through the skin of the subject wearing the wearable apparatus. Moreover, each of the example ERPMs provided hereinbelow are formulated to be capable of releasing the respective bio-active agent(s) comprised in the bio-active solution at a therapeutically effective rate through transdermal absorption for a period of at least three months.

Example 1—Polyolefin Elastomer-Based Joint Health ERPM

An example "Joint health" ERPM comprising glucosamine, chondroitin sulfate, and methylsulfonylmethane (MSM) as the bio-active ingredients and a carrier liquid comprising ESBO was formulated as follows:

TABLE 1

| Ingredient | Percentage of total (by weight) |
|---|---|
| Structural polymer | |
| Polyolefin elastomer (Dow Engage ™ 8407) | Remainder up to 100% |
| LDPE | 45% to 55% |
| Bio-active ingredient(s) | |
| glucosamine | 7% to 15% |
| chondroitin sulfate | 3% to 7% |
| MSM | 3% to 7% |

TABLE 1-continued

| Ingredient | Percentage of total (by weight) |
|---|---|
| Liquid-binding granules | |
| Fumed silica | 0.5% to 1% |
| Carrier liquid | |
| ESBO | 3% to 5% |
| Lavender essential oil | 0.1% to 0.2% |
| Additional ingredients | |
| Color, lubricant, etc. | 0% to 10% |

The ESBO, lavender essential oil (together forming the carrier liquid) and the fumed silica were mixed together until the carrier liquid was absorbed into the fumed silica to form carrier-infused granules. The carrier-infused granules were then combined with glucosamine, chondroitin sulfate and MSM, respectively in powder form, and the structural polymer (a polyolefin elastomer and an LDPE) in a compounding extruder at a temperature above the melting point of the one or more polyolefins to form a "joint support" ERPM comprising islands of glucosamine, chondroitin sulfate and MSM, embedded within the polyolefin structural polymer. The ERPM was then granulated to form ERPM granules. The ERPM granules were then injection molded into a wristband-shaped mold to form a wristband-shaped wearable apparatus.

Example 2—Polyolefin Elastomer-Based Collagen ERPM

An example collagen ERPM comprising a collagen as the bio-active ingredient, a glycerol as the carrier liquid, and a structural polymer comprising an LDPE and a polyolefin elastomer was formulated as follows:

TABLE 2

| Ingredient | Percentage of total (by weight) |
|---|---|
| Structural polymer | |
| Polyolefin elastomer (Dow Engage ™ 8407) | Remainder up to 100% |
| LDPE | 45% to 55% |
| Bio-active ingredient(s) | |
| Collagen | 5% to 20% |
| Liquid-binding granules | |
| Fumed silica | 0.5% to 1% |
| Carrier liquid | |
| Glycerol | About 5% |
| Additional ingredients | |
| Color, lubricant, etc. | 0% to 10% |

Similar to what was described in Example 1 herein above, the carrier liquid (glycerol) and the liquid-binding granules (fumed silica) were mixed together until the carrier-liquid was absorbed into the liquid-binding granules to form carrier-infused granules. The carrier-infused granules were then combined with the remaining ingredients, including the bio-active ingredient (collagen in powder form) and the structural polymer (polyolefin elastomer), in a compounding extruder at a temperature above the melting point of the structural polymer to form a collagen-embedded ERPM comprising islands of collagen embedded within the structural polymer. The ERPM was then granulated to form ERPM granules. The ERPM granules were then injection molded to form a wearable shape, such as a wristband, necklace, or a collar.

Example 3—Polyolefin Elastomer-Base Curcumin ERPM

An example curcumin ERPM comprising curcumin as the bio-active ingredient, a glycerol as the carrier liquid, and a structural polymer comprising an LDPE and a polyolefin elastomer is formulated as follows:

TABLE 3

| Ingredient | Percentage of total (by weight) |
|---|---|
| Structural polymer | |
| Polyolefin elastomer (Dow Engage ™ 8407) | Remainder up to 100% |
| LDPE | 45% to 55% |
| Bio-active ingredient(s) | |
| curcumin | 2% to 20% |
| Liquid-binding granules | |
| Fumed silica | 0.5% to 1% |
| Carrier liquid | |
| Glycerol | About 5% |
| Additional ingredients | |
| Color, lubricant, etc. | 0% to 10% |

Similarly to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredient (curcumin in powder form) and the structural polymer (polyolefin elastomer), in a compounding extruder at a temperature above the melting point of the structural polymer to form a curcumin-embedded ERPM comprising islands of curcumin embedded within the structural polymer. The ERPM is then granulated to form ERPM granules. The ERPM granules are then injection molded to form a wearable shape, such as a wristband, necklace, or a collar.

It will be appreciated that the bio-active solution released from the curcumin-embedded ERPM is similar and functionally equivalent to a glycerol tincture (glycerite) of turmeric, which is known to be enriched in curcumin. It will also be appreciated that a similar formulation can be applied to make ERPMs embedded with islands of powdered turmeric. It will also be appreciated that a same or similar formulation can be used to make an herbal ERPM comprising, as the bio-active ingredient(s), one or a combination of more than one of various herbal ingredients that are typically used to make glycerites, such as but not limited to burdock root, chamomile, dandelion, echinacea, elderflower, ginger root, goldenseal, hawthorn, mugwort, nettle, ginseng, or valerian.

It will be understood that an herbal ERPM formulation will have a higher relative content of the bio-active ingredient in a case where the bio-active ingredient is a powdered plant matter of an herb, compared to an extract of the same herb that is typically enriched in a desired bio-active agent comprised in the herb.

In some embodiments, ERPMs embedded with islands of powdered herbal ingredients may utilize a carrier liquid comprising a non-volatile oil instead of glycerol. The at least one bio-active ingredient comprised in the islands may be one or a mixture of herbs that are typically used to make an oil-based tincture, such as but not limited lavender, rosemary, ginger root, curcumin, or valerian, in powder form. An example formulation of such an ERPM comprising a non-volatile oil as the carrier liquid and islands of powered herb as the bio-active ingredient is described herein below.

Example 4—Polyolefin Elastomer-Based ERPM Comprising Powdered Lavender

An example "lavender" ERPM comprising powdered lavender as the bio-active ingredient, a non-volatile oil as the carrier, and a structural polymer comprising an LDPE and a polyolefin elastomer is formulated as follows:

TABLE 4

| Ingredient | Percentage of total (by weight) |
|---|---|
| Structural polymer | |
| Polyolefin elastomer (Dow Engage ™ 8407) | Remainder up to 100% |
| LDPE | 45% to 55% |
| Bio-active ingredient(s) | |
| dried lavender powder | 2% to 20% |
| Liquid-binding granules | |
| Fumed silica | 0.5% to 1% |
| Carrier liquid | |
| Paraffin oil | About 5% |
| Lavender essential oil | 0.5% to 1% |
| Additional ingredients | |
| Color, lubricant, etc. | 0% to 10% |

Similar to what was described in the other Examples herein above, the carrier liquid (paraffin oil) and the liquid-binding granules (fumed silica) is mixed together until the carrier-liquid is absorbed into the liquid-binding granules to form carrier-infused granules. The carrier-infused granules are then combined with the remaining ingredients, including the bio-active ingredient (powdered lavender) and the structural polymer (polyolefin elastomer), in a compounding extruder at a temperature above the melting point of the structural polymer to form a lavender-embedded ERPM comprising islands of powdered lavender embedded within the structural polymer. The ERPM was then granulated to form ERPM granules. The ERPM granules were then injection molded to form a wearable shape, such as a wristband, necklace, or a collar.

Example 5—Polyolefin Elastomer-Based Vitamin B12 ERPM

ERPMs may also be used as a vehicle for extended administration of vitamin supplements.

An example ERPMs comprising vitamin B12 as the bio-active ingredient, a carrier liquid comprising ESBO, and a structural polymer comprising an LDPE and a polyolefin elastomer are formulated as follows:

TABLE 5

| Ingredient | Percentage of total (by weight) |
|---|---|
| Structural polymer | |
| Polyolefin elastomer (Dow Engage ™ 8407) | Remainder up to 100% |
| LDPE | 45% to 55% |
| Bio-active ingredient(s) | |
| vitamin B12 | 1% to 7% |
| Liquid-binding granules | |
| Fumed silica | 0.5% to 1% |
| Carrier liquid | |
| ESBO | 3% to 5% |
| chamomile essential oil | 0.1% to 0.2% |
| Additional ingredients | |
| Color, lubricant, etc. | 0% to 10% |

Similar to what was described in the other Examples herein above, the carrier liquid (ESBO and chamomile essential oil) and the liquid-binding granules (fumed silica) are mixed together until the carrier-liquid was absorbed into the liquid-binding granules to form carrier-infused granules. The carrier-infused granules are then combined with the remaining ingredients, including the bio-active ingredient (vitamin B12 in powder form) and the structural polymer (polyolefin elastomer), in a compounding extruder at a temperature above the melting point of the structural polymer to form a B12-embedded ERPM comprising islands of B12 embedded within the structural polymer. The ERPM is then granulated to form ERPM granules. The ERPM granules are then injection molded to form a wearable shape, such as a wristband, necklace, or a collar.

Example 6—TPU-Based Collagen ERPM

Another example collagen ERPM comprising collagen as the bio-active ingredient (and bio-active agent) as well as glycerol as the carrier liquid are formulated as follows:

TABLE 6

| Ingredient | Percentage of total (by weight) |
|---|---|
| Structural polymer | |
| TPU (Estane ® GP 85 AE) | Remainder up to 100% |
| Bio-active ingredient(s) | |
| Collagen | 10% to 20% |
| Liquid-binding granules | |
| Fumed silica | 0.5% to 1% |
| Carrier liquid | |
| Glycerol | 3% to 7% |
| Additional ingredients | |
| Ethylene bis (stearamide) | 0.2% to 1% |
| Color, lubricant, etc. | 0% to 10% |

Similar to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredient (collagen in powder form) and the structural polymer (TPU), in a compounding extruder at a temperature above the melting point of the structural polymer to form a collagen-embedded ERPM comprising islands of collagen embedded within the structural polymer. The ERPM is then granulated to form ERPM granules. The ERPM granules are then injection molded to form a wearable shape, such as a wristband, necklace, or a collar.

The present disclosure also includes an SBS-based formulation for a collagen ERPM, which is identical to the formulation described in table 6 and formulated as described herein above, with the exception that the structural polymer is SBS rubber instead of TPU.

Example 7—PVC-Based Joint Health ERPM

Another example of a "joint health" ERPM comprising glucosamine, chondroitin sulfate, and curcumin as the bio-active ingredients (and agents), glycerol as the carrier liquid, and PVC as the structural polymer was formulated as follows:

TABLE 7

| Ingredient | Percentage of total (by weight) |
|---|---|
| Structural polymer | |
| PVC_(K-67) | Remainder up to 100% |
| Bio-active ingredient(s) | |
| Glucosamine | 10% to 18% |
| Chondroitin sulfate | 3% to 7% |
| Curcumin | 3% to 7% |
| Liquid-binding granules | |
| Fumed silica | 0.5% to 1% |
| Carrier liquid | |
| Glycerol | 3% to 7% |
| ESBO | 1% to 2% |
| Additional ingredients | |
| Di-isononyl adipate | 3% to 7% |
| Di-isononyl phthalate | 8% to 12% |
| Calcium-zinc(CaZn) stabilizer | |
| Stearin | 0.2% to 0.6% |
| Color, lubricant, etc. | 0% to 5% |

Similar to what was described in the other Examples herein above, the carrier liquid (glycerol) and the liquid-binding granules (fumed silica) were mixed together until the carrier-liquid was absorbed into the liquid-binding granules to form carrier-infused granules. The carrier-infused granules were then combined with the remaining ingredients, including the bio-active ingredient (glucosamine, chondroitin sulfate, and curcumin, respectively in powder form) and the structural polymer (PVC), in a compounding extruder at a temperature above the melting point of the structural polymer to form a joint health ERPM comprising islands of glucosamine, chondroitin sulfate, and curcumin embedded within the structural polymer. The ERPM was then granulated to form ERPM granules. The ERPM granules were then injection molded to form a wearable shape, such as a wristband, necklace, or a collar.

Example 8—TPU-Based Calming ERPM

An example "calming" ERPM comprising relaxation-inducing bio-active ingredients, glycerol as the carrier liquid and a structural polymer comprising TPU is formulated as follows:

TABLE 8

| Ingredient | Percentage of total (by weight) |
|---|---|
| Structural polymer | |
| TPU (Estane ® GP 85 AE) | Remainder up to 100% |
| Bio-active ingredient(s) | |
| 5-Hydroxytryptophan | 4% to 8% |
| Saffron extract | 4% to 8% |
| Hypericum extract | 3% to 7% |
| Liquid-binding granules | |
| Fumed silica | 0.5% to 1% |
| Carrier liquid | |
| Glycerol | 3% to 7% |
| Additional ingredients | |
| Ethylene bis (stearamide) | 0.2% to 1% |
| Color, lubricant, etc. | 0% to 10% |

Similar to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredients (5-Hydroxytryptophan, saffron extract, and hypericum extract, each in powder form) and the structural polymer (TPU), in a compounding extruder at a temperature above the melting point of the structural polymer to form a "calming" ERPM comprising islands of 5-Hydroxytryptophan, saffron extract, and hypericum extract embedded within the structural polymer. The ERPM is then granulated to form ERPM granules. The ERPM granules are then injection molded to form a wearable shape, such as a wristband, necklace, or a collar.

The present disclosure also includes an SBS-based formulation for a collagen ERPM, which is identical to the formulation described in table 6 and formulated as described herein above, with the exception that the structural polymer is SBS rubber instead of TPU.

Example 9—Thermoplastic Elastomer-Based Calming ERPM

Another example "calming" ERPM comprising relaxation-inducing bio-active ingredients, glycerol as the carrier liquid and a structural polymer comprising an LDPE and a polyolefin elastomer is formulated as follows:

TABLE 9

| Ingredient | Percentage of total (by weight) |
|---|---|
| Structural polymers | |
| Polyolefin elastomer (Dow Engage ™ 8407) | Remainder up to 100% |
| LDPE | 45% to 55% |
| Bio-active ingredient(s) | |
| 5-Hydroxytryptophan | 4% to 8% |
| Saffron extract | 4% to 8% |
| Hypericum extract | 3% to 7% |
| Liquid-binding granules | |
| Fumed silica | 0.5% to 1% |

TABLE 9-continued

| Ingredient | Percentage of total (by weight) |
|---|---|
| Carrier liquid | |
| Glycerol | 3% to 7% |
| Additional ingredients | |
| Color, lubricant, etc. | 0% to 10% |

Similar to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredients (5-Hydroxytryptophan, saffron extract, and hypericum extract, each in powder form) and the structural polymer (a combination of an LDPE and an Engage™ polyolefin from Dow), in a compounding extruder at a temperature above the melting point of the structural polymer to form a "calming" ERPM comprising islands of 5-Hydroxytryptophan, saffron extract, and hypericum extract embedded within the structural polymer. The ERPM is then granulated to form ERPM granules. The ERPM granules are then injection molded to form a wearable shape, such as a wristband, necklace, or a collar.

Example 10—TPU-Based Energy ERPM

An example "energy" ERPM comprising glycerol as the carrier liquid and a structural polymer comprising TPU is formulated as follows:

TABLE 10

| Ingredient | Percentage of total (by weight) |
|---|---|
| Structural polymer | |
| TPU (Estane ® GP 85 AE) | Remainder up to 100% |
| Bio-active ingredient(s) | |
| L-arginine | 8% to 12% |
| L-citrulline | 5% to 9% |
| Liquid-binding granules | |
| Fumed silica | 0.5% to 1% |
| Carrier liquid | |
| Glycerol | 3% to 7% |
| Additional ingredients | |
| Ethylene bis (stearamide) | 0.2% to 0.6% |
| Color, lubricant, etc. | 0% to 10% |

Similar to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredients (L-arginine and L-citrulline, each in powder form) and the structural polymer (a TPU), in a compounding extruder at a temperature above the melting point of the structural polymer to form an "energy" ERPM comprising islands of L-arginine and L-citrulline embedded within the structural polymer. The ERPM is then granulated to form ERPM granules. The ERPM granules are then injection molded to form a wearable shape, such as a wristband, necklace, or a collar.

The present disclosure also includes an SBS-based formulation for an energy ERPM, which is identical to the formulation described in table 6 and formulated as described herein above, with the exception that the structural polymer is SBS rubber instead of TPU.

Example 11—Polyolefin Elastomer-Based Energy ERPM

Another example "energy" ERPM, comprising glycerol as the carrier liquid and a structural polymer comprising an LDPE and a polyolefin elastomer is formulated as follows:

TABLE 11

| Ingredient | Percentage of total (by weight) |
|---|---|
| Structural polymers | |
| Polyolefin elastomer (Dow Engage ™ 8407) | Remainder up to 100% |
| LDPE | 45% to 55% |
| Bio-active ingredient(s) | |
| L-arginine | 8% to 12% |
| L-citrulline | 5% to 9% |
| Liquid-binding granules | |
| Fumed silica | 0.5% to 1% |
| Carrier liquid | |
| Glycerol | 3% to 7% |
| Additional ingredients | |
| Ethylene bis (stearamide) | 0.2% to 0.6% |
| Color, lubricant, etc. | 0% to 10% | to what was described in the other Examples herein above, the carrier liquid (glycerol) and the liquid-binding granules (fumed silica) are mixed together until the carrier-liquid is absorbed into the liquid-binding granules to form carrier-infused granules. The carrier-infused granules are then combined with the remaining ingredients, including the bio-active ingredients (L-arginine and L-citrulline, each in powder form) and the structural polymer (a combination of an LDPE and an Engage™ polyolefin from Dow), in a compounding extruder at a temperature above the melting point of the structural polymer to form an "energy" ERPM comprising islands of L-arginine and L-citrulline embedded within the structural polymer. The ERPM is then granulated to form ERPM granules. The ERPM granules are then injection molded to form a wearable shape, such as a wristband, necklace, or a collar.

Example 12—Polyolefin Elastomer-Based Joint Health ERPM

Another example of a joint health ERPM comprising glucosamine, chondroitin sulfate, and methylsulfonylmethane (MSM) as the bio-active ingredients, glycerol as the carrier liquid, and structural polymer comprising a polyolefin elastomer was formulated as follows:

TABLE 12

| Ingredient | Percentage of total (by weight) |
|---|---|
| Structural polymer | |
| Polyolefin elastomer (Dow Engage ™ 8407) | Remainder up to 100% |
| LDPE | 45% to 55% |

TABLE 12-continued

| Ingredient | Percentage of total (by weight) |
|---|---|
| Bio-active ingredient(s) | |
| glucosamine | 7% to 15% |
| chondroitin sulfate | 3% to 7% |
| MSM | 3% to 7% |
| Liquid-binding granules | |
| Fumed silica | 0.5% to 1% |
| Carrier liquid | |
| glycerol | 3% to 5% |
| Additional ingredients | |
| Color, lubricant, etc. | 0% to 10% |

The fumed silica and a first volume of the glycerol were mixed together until the glycerol was absorbed into the fumed silica to form carrier-infused granules. MSM was dissolved in a second volume of the glycerol at about a 2:1 (MSM:glycerol) ratio by weight at a temperature of between 50 deg. C and 60 deg. C to form an MSM-glycerol solution. The carrier-infused granules and the MSM-glycerol solution were combined with the remaining ingredients, including the glucosamine and chondroitin sulfate, respectively in powder form along with the polyolefin elastomer, in a compounding extruder at a temperature above the melting point of the polyolefin elastomer to form a "joint support" ERPM. The ERPM was cooled and then granulated to form ERPM granules. The ERPM granules are then injection molded to form a wearable shape, such as a wristband, necklace, or a collar. Once the ERPM returns to room temperature, most of the MSM that was previously dissolved in glycerol returns to solid form as precipitates within the structural polymer matrix. As such, the joint support ERPM wristband comprises islands of glucosamine, chondroitin sulfate and MSM embedded within the polymer matrix.

In the Examples herein above comprising a polyolefin elastomer (such as Examples 1-5, 9, 11 and 12), the formulations presented in the respective tables used Dow Engage™ 8407, an ethylene-octene elastomer, as the polyolefin elastomer. However, other polyolefin elastomers were also used in, or contemplated for, alternative formulations, including Dow Engage™ 8137 (another ethylene-octene elastomer), as well as Dow Engage™ 11527 (an ethylene-butene elastomer), and Sabic Fortify™ 300700D. Other appropriate polyolefin elastomers, including ethylene-butene, ethylene-hexene, and ethylene-octene elastomers, may be selected based on the guidance provided herein to achieve a desired physical property, such as elasticity and melting point. In addition, LDPE was used in combination with the polyolefin elastomer primarily due to reasons of cost and ready availability compared to the polyolefin elastomers. It is expected that alternative formulations for Examiners 1-5, 9, 11 and 12 that use primarily or only polyolefin elastomers, with little or no LDPE, would also provide an ERPM 20 with the above-noted extended-release properties.

Example 13—Treatment of Dogs Diagnosed with Osteoarthritis with a Joint Support ERPM Collar as Described in One of Examples 1, 7 or 12

An efficacy study is conducted in 20 animals (dogs). Over 120 days, 10 experimental animals wear a joint support ERPM (JS-ERPM) collar, produced with the formulation described herein above in Example 12, and 10 control animals wear a placebo collar. All animals (experimental and control) participating in the experiment are selected based on being previously diagnosed with osteoarthritis. On Day 0 (one day before application of the collars), Day 30, Day 60, Day 90 and Day 120 of the study, each animal in each study groups undergo the following examinations: Ultra Sound examination in problematic zones; WOMAC (Western Ontario and McMaster Universities Osteoarthritis Index) score examination adapted for dogs, used to evaluate the condition of subjects with osteoarthritis including pain, stiffness, and physical functioning of the joints; General veterinary observation for joint mobility, lameness, pain on palpation, clinical signs; and measuring Calcium/Phosphorus (Ca/P) ratio in blood.

It is found that the experimental animals wearing the JS-ERPM collar exhibit substantial relief from osteoarthritis symptoms starting from the first post-collar-application examination conducted at Day 30, as indicated by ultrasound, the WOMAC store, general veterinary observation and the Ca/P ratio. The osteoarthritis relief in the experimental group persists throughout the study period of 120 days, indicating that the JS-ERPM collar will continue to provide relief from osteoarthritis symptoms beyond the 120-day study period. There are no adverse reactions presented by any of the experimental animals treated with the JS-ERPM collar. By contrast, the osteoarthritis symptoms persist unchanged in control animals throughout the 120-day study period.

Example 14—Treatment of Cats Diagnosed with Osteoarthritis with a Joint Support ERPM Collar as Described in One of Examples 1, 7 or 12

An efficacy study is conducted in 20 animals (cats). Over 120 days, 10 experimental animals wear a joint support ERPM (JS-ERPM) collar, produced with the formulation described herein above in Example 12, and 10 control animals wear a placebo collar. All animals (experimental and control) participating in the experiment are selected based on being previously diagnosed with osteoarthritis. On Day 0 (one day before application of the collars), Day 30, Day 60, Day 90 and Day 120 of the study, each animal in each study groups undergo the following examinations: Ultra Sound examination in problematic zones; WOMAC (Western Ontario and McMaster Universities Osteoarthritis Index) score examination adapted for cats, used to evaluate the condition of subjects with osteoarthritis including pain, stiffness, and physical functioning of the joints; General veterinary observation for joint mobility, lameness, pain on palpation, clinical signs; and measuring Calcium/Phosphorus (Ca/P) ratio in blood.

It is found that the experimental animals wearing the JS-ERPM collar exhibit substantial relief from osteoarthritis symptoms starting from the first post-collar-application examination conducted at Day 30, as indicated by ultrasound, the WOMAC store, general veterinary observation and the Ca/P ratio. The osteoarthritis relief in the experimental group persists throughout the study period of 120 days, indicating that the JS-ERPM collar will continue to provide relief from osteoarthritis symptoms beyond the 120-day study period. There are no adverse reactions presented by any of the experimental animals treated with the JS-ERPM collar. By contrast, the osteoarthritis symptoms persist unchanged in control animals throughout the 120-day study period.

There is therefore provided a plastic material for extended release of a bio-active agent, the plastic material comprising: a structural polymer; at least one bio-active ingredient embedded within the structural polymer as solid islands; a liquid binding material embedded within the structural polymer as granules; and a carrier liquid absorbed within the liquid-absorbent material.

In an embodiment of the disclosure, the carrier liquid is sufficiently non-compatible with the structural polymer so that at least a portion of the carrier liquid is released from the liquid-absorbent material through the structural polymer to an outer surface of the plastic material over a period of time. Optionally, the period of time is at least a week, at least a month, or at least three months.

In an embodiment of the disclosure, a bio-active agent comprised in the at least one bio-active ingredient is sufficiently soluble in the carrier liquid at room or body temperature so that the carrier liquid released to the outer surface comprises the bio-active agent in solution.

In an embodiment of the disclosure, the structural polymer comprises a polyolefin. In an embodiment of the disclosure, the structural polymer comprises one or a combination or two or more selections from the group consisting of: a polyolefin elastomer, a polyethylene (PE), a polyvinyl chloride (PVC), a polyurethane (PU), an ethylene vinyl acetate (EVA), and a synthetic rubber. Optionally, the polyethylene comprises one or a combination or two or more selections from the group consisting of: a low-density polyethylene (LDPE), and a linear low-density polyethylene (LLDPE). Optionally, the structural polymer is formulated to be hydrophobic.

In an embodiment of the disclosure, the liquid binding material is selected from the group consisting of: a silica gel, a fumed silica, a diatomite, a carbon black, and an activated carbon.

In an embodiment of the disclosure, the liquid binding material comprises a porous polymer. Optionally, the melting point of the porous polymer is higher than the melting point of the structural polymer.

In an embodiment of the disclosure, the carrier liquid comprises a non-volatile oil. Optionally, the non-volatile oil is a paraffin oil or a plant-derived oil.

In an embodiment of the disclosure, the liquid comprises one or a combination of two or more selections from the group consisting of: a chlorinated paraffin, a triacetin, a naphtenic hydrocarbon, an aliphatic hydrocarbon, a dioctyl terephthalate (DOTP), a diisononyl phthalate (DINP), and an epoxidized triglyceride.

In an embodiment of the disclosure, the carrier liquid comprises a glycerol.

In an embodiment of the disclosure, the solid islands of the at least bio-active ingredient consists of the bio-active agent in a purified form.

In an embodiment of the disclosure, the solid islands of the at least one bio-active ingredient comprises a natural product that is a mixture of the bio-active agent and materials that are not soluble in the carrier liquid. Optionally, the solid islands of the at least one bio-active ingredient comprises a powdered plant matter.

In an embodiment of the disclosure, the solid islands of the at least one bio-active ingredient comprises an extract prepared from a plant matter.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which the embodiment is intended. Wherever a general term in the disclosure is illustrated by reference to an example instance or a list of example instances, the instance or instances referred to, are by way of non-limiting example instances of the general term, and the general term is not intended to be limited to the specific example instance or instances referred to. Unless otherwise indicated, the word "or" in the description and claims is considered to be the inclusive "or" rather than the exclusive or, and indicates at least one of, or any combination of more than one of items it conjoins.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments. Some embodiments utilize only some of the features or possible combinations of the features. Variations of embodiments of the disclosure that are described, and embodiments comprising different combinations of features noted in the described embodiments, will occur to persons of the art. The scope of the invention is limited only by the claims.

The invention claimed is:

1. A method for transdermal delivery of a bio-active agent to the skin of an animal or human, comprising;
    contacting a device to the skin of the animal or human, wherein the device comprises:
        a structural polymer comprising an olefin;
        at least one bio-active ingredient embedded within the structural polymer as solid islands;
        a liquid-binding material embedded within the structural polymer as granules; and
        a carrier liquid absorbed within the liquid-binding material,
        wherein the carrier liquid is sufficiently non-compatible with the structural polymer so that at least a portion of a carrier liquid solution comprising bio-active agent dissolved in the carrier liquid released from the liquid binding material moves through the structural polymer to an outer surface of the structural polymer over a period of time.

2. The method according to claim 1, wherein the bio-active agent is released at a therapeutically effective rate in the context of transdermal absorption.

3. The method according to claim 1, wherein the bio-active agent comprised in the at least one bio-active ingredient is sufficiently soluble in the carrier liquid at room or body temperature so that the carrier liquid released to the outer surface comprises the bio-active agent in solution.

4. The method according to claim 1, wherein the period of time is at least a month.

5. The method according to claim 1, wherein the period of time is at least three months.

6. The method according to claim 1, wherein the carrier liquid solution is selectively released at portions of the outer surface of the structural polymer in contact with the outer dermal surface.

7. The method according to claim 1, wherein the polyolefin comprises one or a combination of two or more selections from the group consisting of a polyolefin elastomer, a polyethylene (PE), a polyvinyl chloride (PVC), a polyurethane (PU), an ethylene vinyl acetate (EVA), and a synthetic rubber.

8. The method according to claim 7, wherein the polyethylene comprises one or a combination of two or more selections from the group consisting of a low-density polyethylene (LDPE), and a linear low-density polyethylene (LLDPE).

9. The method according to claim 1, wherein the structural polymer is hydrophobic.

10. The method according to claim 1, wherein the liquid-binding material is selected from the group consisting of a silica gel, a fumed silica, a diatomite, a carbon black, and an activated carbon.

11. The method according to claim 1, wherein the liquid-binding material comprises a porous polymer.

12. The method according to claim 11, wherein the melting point of the porous polymer is higher than the melting point of the structural polymer.

13. The method according to claim 1, wherein the carrier liquid comprises a non-volatile oil.

14. The method according to claim 13, wherein the non-volatile oil is a paraffin oil or a plant-derived oil.

15. The method according to claim 13, wherein the carrier liquid comprises one or a combination of two or more selections from the group consisting of a chlorinated paraffin, a triacetin, a naphtenic hydrocarbon, an aliphatic hydrocarbon, a dioctyl terephthalate (DOTP), a diisononyl phthalate (DINP), and an epoxidized triglyceride.

16. The method according to claim 13, wherein the carrier liquid comprises a glycerol.

17. The method according to claim 1, wherein the solid islands of the at least bio-active ingredient consists of the bio-active agent in a purified form.

18. The method according to claim 1, wherein the solid islands of the at least one bio-active ingredient comprise a natural product that is a mixture of the bio-active agent and materials that are not soluble in the carrier liquid.

19. The method according to claim 18, wherein the solid islands of the at least one bio-active ingredient comprise a powdered plant matter.

20. The method according to claim 1, wherein the solid islands of the at least one bio-active ingredient comprise an extract prepared from a plant matter.

* * * * *